US008501800B2

(12) United States Patent
Bowman et al.

(10) Patent No.: US 8,501,800 B2
(45) Date of Patent: Aug. 6, 2013

(54) CONTROLLED-RELEASE OPHTHALMIC VEHICLES

(75) Inventors: Lyle Bowman, Pleasanton, CA (US); Stephen Pham, Sacramento, CA (US)

(73) Assignee: Insite Vision Incorporated, Alameda, CA (US)

( * ) Notice: Subject to any disclaimer, the term of this patent is extended or adjusted under 35 U.S.C. 154(b) by 0 days.

(21) Appl. No.: 12/398,625

(22) Filed: Mar. 5, 2009

(65) Prior Publication Data

US 2010/0226997 A1    Sep. 9, 2010

(51) Int. Cl.
*A61K 38/00* (2006.01)
*A61K 38/28* (2006.01)
*A61K 31/40* (2006.01)

(52) U.S. Cl.
USPC ............... 514/419; 514/54; 514/62; 514/912

(58) Field of Classification Search
USPC ..................... 514/54, 62, 419, 912
See application file for complete search history.

(56) References Cited

U.S. PATENT DOCUMENTS

| 2,798,053 | A |   | 7/1957  | Brown |
|---|---|---|---|---|
| 4,136,250 | A |   | 1/1979  | Mueller et al. |
| 4,192,827 | A |   | 3/1980  | Mueller et al. |
| 4,548,990 | A |   | 10/1985 | Mueller et al. |
| 5,188,826 | A | * | 2/1993  | Chandrasekaran et al. .................. 424/78.04 |
| 5,192,535 | A | * | 3/1993  | Davis et al. ............... 424/78.04 |
| 7,303,748 | B2 | * | 12/2007 | Wiegand et al. ........... 424/134.1 |

FOREIGN PATENT DOCUMENTS

| EP | 1 911 447 A1    | 4/2008 |
|---|---|---|
| WO | WO 2007/042262 A2 | 4/2007 |

OTHER PUBLICATIONS

Shulman et al., "Comparative evaluation of the short-term bactericidal potential of a steroid-antibiotic combination versus steroid in the treatment of chronic bacterial blepharitis and conjunctivitis," European Journal of Ophthalmology, vol. 6, No. 4, (1996) pp. 361-367.

Wagh, V. D. et al., "Formulation and evaluation of ophthalmic insert drug delivery system of forskolin," Asian Journal of Pharmaceutics, Oct.-Dec. 2008, pp. 221-224.

Saettone et al., "Evaluation of muco-adhesive properties and in vivo activity of ophthalmic vehicles based on hyaluronic acid," International Journal of Pharmaceutics, vol. 51, No. 3 (May 1, 1989) pp. 203-212.

Bucci. Jr, F.A. et al., "Comparison of ketorolac 0.4% and bromfenac 0.09% at trough dosing: Aqueous drug absorption and prostaglandin E2 levels," J Cataract Refract Surg, vol. 34, Sep. 2008, pp. 1509-1512.

Baklayan et al., 24-Hour Evaluation of the Ocular Distribution of 14C-Labeled Bromfenac Following Topical Instillation into the Eyes of New Zealand White Rabbits, Journal of Ocular Pharmacology and Therapeutics, vol. 24, No. 4, 2008, pp. 392-398.

International Search Report and Written Opinion of the International Searching Authority issued in International Patent Application No. PCT/US2010/026347, mailed Nov. 10, 2010.

Kao, H.J., et al., "Characterization of pilocarpine-loaded chitosan/Carbopol nanoparticles", Journal of Pharmacy and Pharmacology, 2006, pp. 179-186, vol. 58 No. 2.

Hu, Y., et al., "Synthesis and characterization of chitosan-poly(acrylic acid) nanoparticles", Biomaterials, 2002, pp. 3193-3201, vol. 23.

* cited by examiner

*Primary Examiner* — Zohreh Fay
(74) *Attorney, Agent, or Firm* — McDermott Will & Emery LLP

(57) ABSTRACT

An ophthalmically acceptable vehicle includes an aqueous suspension having a first viscosity. The suspension includes about 0.1% to about 6.5% by weight of a carboxyl-containing polymer prepared by polymerizing one or more carboxyl-containing monoethylenically unsaturated monomers and less than about 5% by weight of a cross-linking agent. The polymer has average particle size of not more than about 50 μm in equivalent spherical diameter. The vehicle includes a second polymer that allows the carboxyl-containing polymer to remain suspended. Upon contact with tear fluid, the vehicle gels to a second viscosity which is greater than the first viscosity. A method of administering a medicament to the eye of a subject includes applying a composition that includes this ophthalmically acceptable vehicle and a medicament contained for treatment of a disease or disorder for which ophthalmic delivery is indicated. The medicament is released from the vehicle in a sustained release manner.

17 Claims, 1 Drawing Sheet

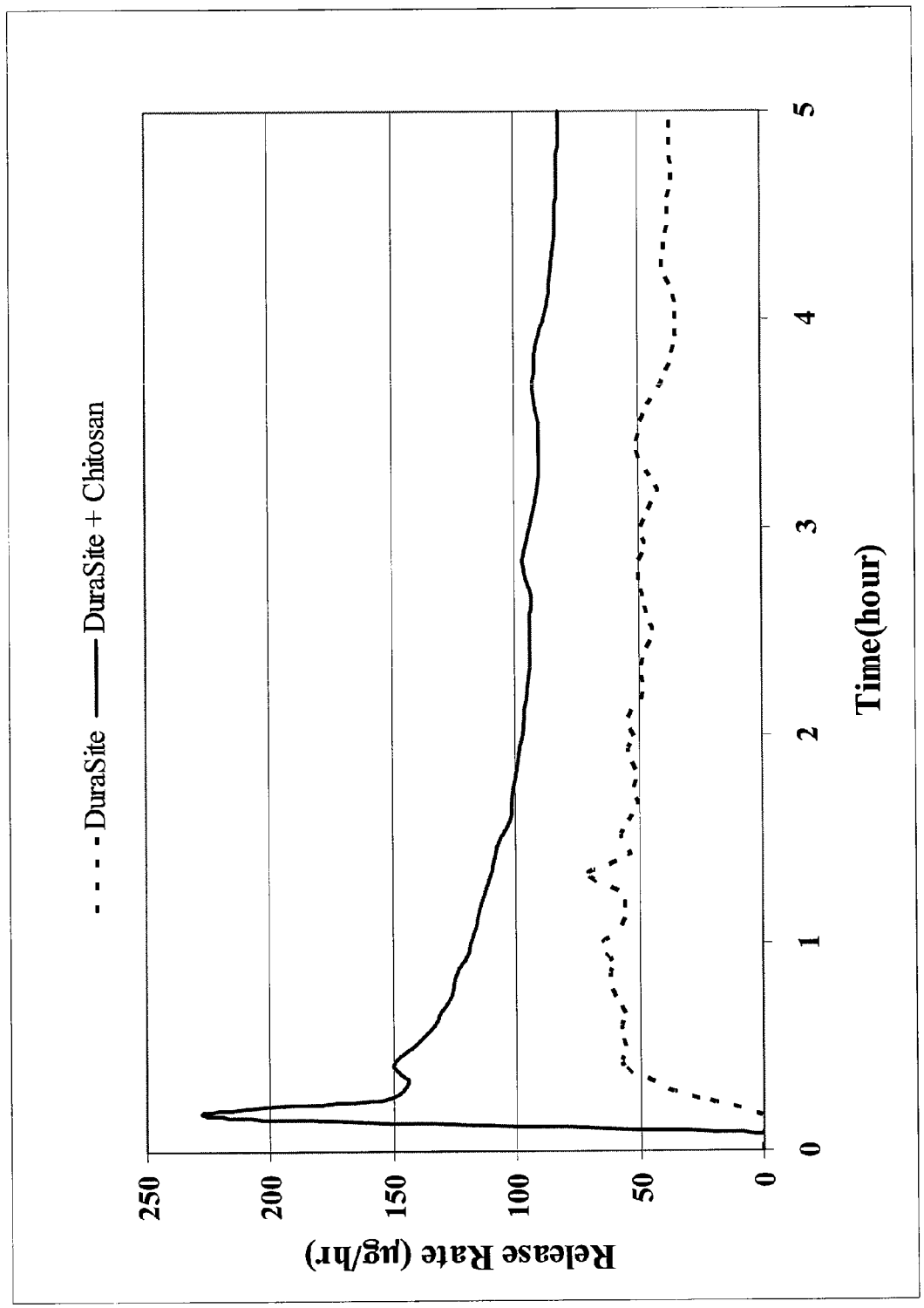

CONTROLLED-RELEASE OPHTHALMIC VEHICLES

BACKGROUND OF THE INVENTION

This invention relates generally to ophthalmic vehicle compositions and, more specifically, to controlled-release ophthalmic vehicle compositions.

Several factors bear consideration in the development of ophthalmic vehicles for delivering a medicament to the eye including patient comfort, consistency and accuracy of dosage, type and time of any vision interference, and ease of administration.

From a delivery perspective, further challenges include formulating ophthalmic vehicles at viscosities low enough for reliable administration in drop form without impacting delivery efficiency and, at the same time, maintaining sufficient viscosity and mucoadhesion so that the delivered medicament remains in or on the eye for a sufficient period of time to effectively treat the affected eye. Moreover, drug delivery to the ocular mucosa faces the additional obstacle of various clearance mechanisms present in the eye.

Thus, there exists a continuing need for improved ophthalmic vehicles that can enhance delivery to and retention of medicaments in the eye and provide sufficient convenience to enhance patient compliance. The present invention satisfies these needs and provides related advantages as well.

SUMMARY OF THE INVENTION

In some aspects, embodiments disclosed herein relate to an ophthalmically acceptable vehicle that includes an aqueous suspension having a first viscosity. The suspension includes from about 0.1% to about 6.5% by weight, based on the total weight of the suspension, of a carboxyl-containing polymer prepared by polymerizing one or more carboxyl-containing monoethylenically unsaturated monomers and less than about 5% by weight of a cross-linking agent. The weight percentages of monomers are based on the total weight of monomers polymerized. The carboxyl-containing polymer has an average particle size of not more than about 50 μm in equivalent spherical diameter. The vehicle also includes a sufficient amount of a second polymer that allows the carboxyl-containing polymer to remain suspended. Upon contact with tear fluid, the vehicle gels to a second viscosity which is greater than the first viscosity.

In other aspects, embodiments disclosed herein relate to a method of administering a medicament to the eye of a subject that includes applying to the eye of a subject a composition including the ophthalmically acceptable aforementioned vehicle and a medicament contained therein for treatment of a disease or disorder for which ophthalmic delivery is indicated. The medicament is released from the vehicle in a sustained release manner.

BRIEF DESCRIPTION OF THE DRAWINGS

FIG. 1 shows the effect of chitosan on release rate of azithromycin from DuraSite.

DETAILED DESCRIPTION OF THE INVENTION

This invention is directed, in part, to an ophthalmic vehicle with desirable rheological properties that are conducive to medicament delivery into the eye and provide corneal retention. The vehicle uses a combination of an anionic carboxy-containing polymer in conjunction with a substantially smaller amount of a second polymer, for example, a cationic polymer. The second polymer is included at a sufficiently low concentration such that the particles of the carboxy-containing polymer remain suspended, yet when combined with the second polymer, the resulting vehicle has higher viscosity than the vehicle with the carboxy-containing polymer alone. The vehicle disclosed herein has the property that, when combined with tear fluid, its viscosity increases due to the higher pH of tear fluid. The resultant viscosity provides a means by which to increase the efficiency of medicament delivery and corneal retention.

The ophthalmically acceptable vehicle disclosed herein also has suitable mucoadhesive properties that can facilitate the absorption of poorly absorbed drugs by increasing the contact time of the drug with the ocular mucosa. Interactions between the vehicle and the ocular mucosa can include Van der Waals attractive forces, hydrogen bonding, and electrostatic interactions between the mucins of the ocular mucosa and the carboxy-containing polymer and the second polymer. Together, these forces can increase the residence time of a medicament in the eye. An additional benefit of the ophthalmically acceptable vehicle disclosed herein, is the ability to provide the medicament in a sustained release manner.

In one embodiment, the invention provides an ophthalmically acceptable vehicle that includes an aqueous suspension containing from about 0.1% to about 6.5% by weight, based on the total weight of the suspension, of a carboxyl-containing polymer prepared by polymerizing one or more carboxyl-containing monoethylenically unsaturated monomers and less than about 5% by weight of a crosslinking agent. The weight percentages of monomers are based on the total weight of monomers polymerized. The carboxyl-containing polymer has an average particle size of not more than about 50 μm in equivalent spherical diameter and is lightly cross-linked.

The vehicle further includes a second polymer, such as a cationic polymer, added in sufficient amount to increase the vehicle viscosity without the loss of polymer particle suspension, while still allowing the vehicle to be administered to the eye in drop form. Upon contact of the lower pH vehicle with higher pH tear fluid, the vehicle rapidly gels to a greater viscosity and therefore can remain in the eye for sustained release of a medicament contained within the vehicle.

As used herein an "ophthalmically acceptable vehicle" is one which allows delivery of a medicament to the eye and/or eyelids, to treat an ocular disease or condition without deleterious effects on the eye. An ophthalmically acceptable vehicle is one that can maintain proper intraocular pressure and provide solutions of medicaments that are isotonic, mildly hypotonic, or mildly hypertonic. To maintain such conditions one can include various non-ionic osmolality-adjusting compounds such as polyhydric alcohols, including for example, glycerol, mannitol, sorbitol, or propylene glycol. Alternatively, osmolality adjusting compounds can include ionic salts such as sodium or potassium chloride. An ophthalmically acceptable vehicle can also include buffers to adjust the vehicle to an acceptable pH, which can range from about 3 to 6.5, and in some embodiments from about 4 to 8, including any pH in between. Such buffer systems include, but not limited to, acetate buffers, citrate buffers, phosphate buffers, borate buffers and mixtures thereof. Specific buffer components useful in the present invention include, but not limited to, citric acid/sodium citrate, boric acid, sodium borate, sodium phosphates, including mono, di- and tri-basic phosphates, such as sodium phosphate monobasic monohydrate and sodium phosphate dibasic heptahydrate, and mixtures thereof. It should be noted that any other suitable ophthalmically acceptable buffer components can be employed to maintain the pH of the ophthalmic formulation so that the ophthalmic formulation is provided with an acceptable pH, and the foregoing buffer components are merely exemplary examples of such buffer components.

As used herein, the term "carboxyl-containing polymer" refers to a polymer that contains the carboxylic acid functional group. This functional group can be substantially ionized, for example, and exist as a carboxylate anion ($COO^-$), rendering the polymer negatively charged. In the context of the ophthalmically acceptable vehicle, the degree of ionization can depend on the pH, which is mediated by any buffer system, and the presence other components in the vehicle that contain Lewis basic atoms, such as an amine-functionalized polymer. A Lewis base is donor of a pair of electrons and as such, is capable of accepting hydrogen ion ($H^+$) from a carboxyl group (COOH).

As used herein, the term "cationic polymer" refers to a positively-charged, amine-functionalized polymer. The polymer contains nitrogen atoms that are quaternized or capable of being quaternized upon adjustment to a sufficiently low pH and/or in the presence of a proton donor, such as the carboxyl containing polymer, or other Lewis acid (i.e. an electron pair acceptor). A quaternized nitrogen atom is a nitrogen atom engaged in bonding to four other atoms, thus causing nitrogen to have a net formal charge of plus one (+1). Examples of nitrogen atoms carrying positive charge include, but not limited to, $NR_4^+$, $NR_3H^+$, $NR_2H^+$, $NRH_2^+$, wherein R can represent any atom or group of atoms bonded to nitrogen.

As used herein "viscosity" refers to a fluid's resistance to flow. The unit of viscosity is dyne second per square centimeter [$dyne·s/cm^2$], or poise [P]. This type of viscosity is also called dynamic viscosity, absolute viscosity, or simple viscosity. This is distinguished from kinematic viscosity which is the ratio of the viscosity of a fluid to its density.

As used herein "mucoadhesive" or "mucoadhesion" refers to the ability of the ophthalmically acceptable vehicle to adhere to the ocular mucosa. Mucoadhesive agents used in the invention include carboxy-containing polymers capable of forming hydrogen bonds. Mucoadhesion can depend on pH and the density of hydrogen bonding groups. In the vehicle of the present invention, the density of cross-linking in the carboxy-containing polymer can affect mucoadhesion. Thus, a lightly cross-linked polymer system has sufficient flexibility to form multiple hydrogen bonds, making it a good mucoadhesive agent. Another vehicle component that can affect mucoadhesion is the second polymer, which can interact with the carboxy-containing polymer, as explained further below.

As used herein, "administered to the eye" means that an ophthalmically acceptable vehicle, along with a medicament, is in the form of an eye drop that can be applied directly to the surface of the eye and/or in the eyelid margins, such administration techniques being familiar to persons skilled in the art.

As used herein, "an effective amount" when used in connection with treating an ocular disease or condition is intended to qualify the amount of a medicament used in the treatment of a particular ocular disease or condition. This amount will achieve the goal of preventing, reducing, or eliminating the ocular disease or condition. An effective amount depends on the particular active ingredient to be administered, although ophthalmic formulations can include, for example, from about 0.05% to about 5.0% by weight, while in other embodiments the active ingredient is present in a range from about 0.08% to about 0.12% by weight. 0.01 mg/ml to 100 mg/ml per dose in one embodiment and from about 1 to 50 mg/ml dose in another embodiment. An "effective amount" can include a dose regimen once per day, twice per day, thrice per day, and so on.

As used herein "medicament" refers to the primary compound responsible for reducing, preventing, or eliminating the clinical signs and symptoms of an ocular disease.

As used herein "an ophthalmically acceptable salt" will include those that exhibit no deleterious effects on the eye as well as being compatible with the active ingredient itself and the components of the ophthalmically acceptable vehicle. Salts or zwitterionic forms of a medicament can be water or oil-soluble or dispersible. The salts can be prepared during the final isolation and purification of the medicament or separately by adjusting the pH of the appropriate medicament formulation with a suitable acid or base.

In some embodiments, the ophthalmically acceptable vehicle uses carboxy-containing polymers in conjunction with a cationic polymer added in sufficient amount to increase the vehicle viscosity, while still allowing the carboxy-containing polymer particles to remain suspended. The vehicle can be in the form of a gel or liquid drops which release a medicament over time when administered to the eye. The carboxy-containing polymer is about 0.1 to about 6.5% in some embodiments, and, in other embodiments about 1.0 to about 1.3% by weight based on the total weight of the suspension of a cross-linked carboxy-containing polymer. Suitable carboxy-containing polymers are described, for example, in U.S. Pat. No. 5,192,535 to Davis et al. which is hereby incorporated in its entirety by reference. These polymer carriers include lightly crosslinked carboxy-containing polymers (such as polycarbophil, or CARBOPOLS®), dextran, cellulose derivatives, polyethylene glycol 400 and other polymeric demulcents such as polyvinylpyrolidone, polysaccharide gels and GELRITE®. A carboxy-containing polymer system known by the tradename DURASITE®, is a polycarbophil-based sustained release topical ophthalmic delivery system that can also be modified with such polymers disclosed herein.

In accordance with certain embodiments, an ophthalmically acceptable carrier capable of sustained release includes an aqueous suspension at a pH of from about 3 to about 8 and an osmolality of from about 10 to about 400 mOsm/kg containing from about 0.1% to about 6.5% by weight, based on the total weight of the suspension, of a carboxyl-containing polymer prepared by polymerizing one or more carboxyl-containing monoethylenically unsaturated monomers and less than about 5% by weight of a cross-linking agent, such weight percentages of monomers being based on the total weight of monomers polymerized. The suspension can have an initial viscosity of from about 1,000 to about 100,000 centipoises (cps). For example, the viscosity can be in a range from about 1,000 to about 5,000 cps, and in other embodiments from about 5,000 to about 10,000 cps, and in still other embodiments from about 10,000 to about 15,000 cps, and in still further embodiments from about 15,000 to about 20,000 cps, and in yet still further embodiments from about 50,000 to about 100,000 cps, including any values in between these recited values. The carboxy-containing polymer has average particle size of not more than about 50 µm, and in some embodiments, not more than about 30 µm, in equivalent spherical diameter. The polymer is lightly cross-linked to a degree such that although the suspension is administrable in drop form, upon contact of the lower pH suspension with the higher pH tear fluid of the eye, the suspension is gellable to a substantially greater viscosity than the viscosity of the suspension as originally administered in drop form. Accordingly, the resulting more viscous gel can remain in the eye for a prolonged period of time so as to release a medicament contained therein in sustained fashion. These properties remain upon addition of the second polymer to the carboxy-containing aqueous suspension. Without being bound by the theory, the cationic polymer increases the viscosity of the base carboxy-containing aqueous suspension, providing beneficial rheological and mucoadhesive properties.

The carboxy-containing polymer is, in one embodiment, prepared from at least about 50% by weight, and in other embodiments from at least about 90% by weight, of one or more carboxyl-containing monoethylenically unsaturated monomers. The carboxy-containing polymer can be prepared by suspension or emulsion polymerizing acrylic acid and a non-polyalkenyl polyether difunctional cross-linking agent to a particle size of not more than about 50 μm in one embodiment, and not more than about 30 μm, in equivalent spherical diameter, in other embodiments. In one embodiment, the cross-linking agent is divinyl glycol. In other embodiments, up to about 40% by weight of the carboxyl-containing monoethylenically unsaturated monomers can be replaced by one or more non-carboxyl-containing monoethylenically unsaturated monomers containing only physiologically and ophthalmologically innocuous substituents.

The osmolality, in some embodiments, achieved by using a physiologically and ophthalmologically acceptable salt in an amount of from about 0.01% to about 1% by weight, based on the total weight of the suspensions. Exemplary salts include potassium and sodium chlorides and others as defined above.

In some embodiments, in a method of preparing sustained release topical ophthalmically acceptable vehicles, the foregoing suspensions modified with the cationic polymer, are prepared and packaged at the desired viscosity of from 1,000 to about 30,000 cps for administration to the eye in drop form. In one exemplary delivery method, the foregoing suspensions, containing the medicament, are administered to the eye at the initial viscosity in drop form to cause the administered suspension, upon contact with the higher pH tear fluid of the eye, to rapidly gel in situ to a significantly greater viscosity. The more viscous gel remains in the eye for a prolonged period of time so as to release the active ingredient in a sustained fashion.

In contrast to other systems, the present invention provides an ophthalmically acceptable vehicle that not only has the benefit of administration in drop form, but also does not suffer from breakdown limitations due to administration at a viscosity suitable for drops. Through administration at a viscosity such that the suspension can be reliably administered in drop form, but which actually increases when the suspension is so administered, controlled release of the active ingredient is significantly enhanced.

A viscosity substantially over 30,000 cps is not useful for drop formulations; when the viscosity is substantially lower than about 1,000 cps, the ability to gel upon contact with tears can be impeded and ocular retention is reduced. The increased gelation upon contact with the tears occurs with a pH change when a suspension having a pH of from about 3 to about 7.4 and an osmolality of from about 10 to about 400 mOsm/kg, contacts tear fluid, which has a higher pH of about 7.2 to about 8.0. Without being bound by the theory, with the pH increase, the carboxylic acid (COOH) functional group disassociates into carboxylate anions (COO$^-$), Through electrostatic interactions, these carboxylate ions repel each other, causing the polymer to expand. The presence of the trace second polymer in the system can provide additional electrostatic, hydrogen bonding, and possible salt-bridge interactions with the mucins of the ocular mucosa, in addition to providing the initial beneficial viscosity modifying properties to the base vehicle. These chemical interactions result in enhanced controlled release of medicament from the vehicle.

The relationship of cross-linking and particle size can be significant. Because the particles are present in a suspension, the degree of cross-linking is necessarily at a level that avoids substantial dissolution of the polymer. On the other hand, since rapid gelation is achieved at the time of the pH change, the degree of cross-linking is necessarily not so great that gelation is precluded. Moreover, if the polymer particle size is too large, induced swelling can tend to take up voids in the volume between large particles that are in contact with one another, rather than the swelling tending to cause gelation.

In a suspension, particle size can be relevant to comfort. However, it has been found that in the system of the present invention, the small particle size and light cross-linking act synergistically to yield the observed rapid gelation when the pH is raised. Surprisingly, the use of particles greater than 50 μm eliminates the observed gelation when the pH of the vehicle is increased. Moreover, at the 50 μm size, there is also reasonably good eye comfort.

In some embodiments, the particles are not only subject to the upper size limits described above, but also to a narrow particle size distribution. Use of a monodispersion of particles, which aids in good particle packing, yields a maximum increased viscosity upon contact of the suspension with the tears and increases eye residence time. At least about 80% in some embodiments, at least about 90% in other embodiments, and at least about 95% in still other embodiments, of the particles should be within a no more than about 10 μm band of major particle size distribution, and overall (i.e., considering particles both within and outside such band) there should be no more than about 20%, in some embodiments, and no more than about 10%, in other embodiments, and no more than about 5%, in still other embodiments, fines (i.e., particles of a size below 1 μm. In some embodiments, the average particle size is lowered from an upper limit of 50 μm, such as 30 μm, and to even smaller sizes such as 6 μm, such that the band of major particle size distribution is also narrowed, for example to 5 μm. In some embodiments, sizes for particles within the band of major particle distribution are less than about 30 μm, less than about 20 μm in other embodiments, and from about 1 μm to about 5 μm in still other embodiments.

The lightly cross-linked polymers of acrylic acid or related alpha, beta-unsaturated carboxylic acids used in ophthalmically acceptable vehicle are well known in the art. In one embodiment such polymers are prepared from at least about 90%, or about 95%, or about 99.9% by weight, based on the total weight of monomers present, of one or more carboxyl-containing monoethylenically unsaturated monomers. Acrylic acid is a common carboxyl-containing monoethylenically unsaturated monomer, but other unsaturated, polymerizable carboxyl-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), umbellic acid (p-hydroxycoumaric acid), and the like can be used in addition to or instead of acrylic acid.

Such polymers are cross-linked by using a small percentage, i.e., less than about 5%, such as from about 0.5% or from about 0.1% to about 1%, and in other embodiments from about 0.2% to about 1%, based on the total weight of monomers present, of a polyfunctional cross-linking agent. Included among such cross-linking agents are non-polyalkenyl polyether difunctional cross-linking monomers such as divinyl glycol; 2,3-dihydroxyhexa-1,5-diene; 2,5-dimethyl-1,5-hexadiene; divinylbenzene; N,N-diallylacrylamide; N,N-diallylmethacrylamide and the like. Also included are polyalkenyl polyether cross-linking agents containing two or more alkenyl ether groupings per molecule, preferably alkenyl ether groupings containing terminal $H_2$ C=C<groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown U.S. Pat. No. 2,798,053. Diolefinic non-hydrophilic macromeric cross-linking agents having molecular weights of from about 400 to about 8,000, such as insoluble di- and polyacrylates and methacrylates of diols and polyols, diisocyanate-hydroxyalxyl acrylate or methacrylate reaction products, and reaction products of isocyanate terminated prepolymers derived from polyester diols, polyether diols or polysiloxane diols with hydroxyalkylmethacrylates, and the like, can also be used as the cross-linking agents; see, e.g., Mueller et al. U.S. Pat. Nos. 4,192,827 and 4,136,250.

The lightly cross-linked polymers can be made from a carboxyl-containing monomer or monomers as the sole monoethylenically unsaturated monomer present, together with a cross-linking agent or agents. They can also be polymers in which up to about 40%, and in some embodiments, from about 0% to about 20% by weight, of the carboxyl-containing monoethylenically unsaturated monomer or monomers has been replaced by one or more non-carboxyl-containing monoethylenically unsaturated monomers containing only physiologically and ophthalmologically innocuous substituents, including acrylic and methacrylic acid esters such as methyl methacrylate, ethyl acrylate, butyl acrylate, 2-ethylhexylacrylate, octyl methacrylate, 2-hydroxyethyl-methacrylate, 3-hydroxypropylacrylate, and the like, vinyl acetate, N-vinylpyrrolidone, and the like; see Mueller et al. U.S. Pat. No. 4,548,990 for a more extensive listing of such additional monoethylenically unsaturated monomers. In some embodiments, polymers are lightly cross-linked acrylic acid polymers wherein the cross-linking monomer is 2,3-dihydroxyhexa-1,5-diene or 2,3-dimethylhexa-1,5-diene.

Exemplary commercially available lightly cross-linked carboxy-containing polymers useful in the invention include, for example, polycarbophil (available, for example, from BF Goodrich, Cleveland, Ohio), a polyacrylic acid cross-linked with divinyl glycol. Without being bound by theory, this polymer benefits from its mucoadhesive properties which aid in increasing the residence time of the active ingredient in the eye. Other mucoadhesive polymers can be used in conjunction with, or in lieu of the lightly cross-linked polymers disclosed herein, for example, Carbopols such as 934P, 940, 941, 971P, 974P, 980, 981 or hyaluronic acid. The latter has been demonstrated to be an effective mucoadhesive polymer in ocular formulations (Saettone et al. Int. J. Pharm. 51: 203-212, (1989)).

The lightly cross-linked carboxy-containing polymers can be prepared by suspension or emulsion polymerizing the monomers, using conventional free radical polymerization catalysts, to a dry particle size of not more than about 50 μm in equivalent spherical diameter; e.g., to provide dry polymer particles ranging in size from about 1 to about 30 μm, and in other embodiments from about 3 to about 10 μm, in equivalent spherical diameter. In general, such polymers will range in molecular weight estimated to be about 100,000 to about 4,000,000, and in some embodiments, about 2,000,000,000 to about 4,000,000,000.

Aqueous suspensions containing polymer particles prepared by suspension or emulsion polymerization whose average dry particle size is appreciably larger than about 50 μm in equivalent spherical diameter are less comfortable when administered to the eye than suspensions otherwise identical in composition containing polymer particles whose equivalent spherical diameters are, on the average, below about 50 μm. Moreover, above the average 50 μm size, the advantage of substantially increased viscosity after administration is not realized. It has also been discovered that lightly cross-linked polymers of acrylic acid or the like prepared to a dry particle size appreciably larger than about 50 μm in equivalent spherical diameter and then reduced in size, e.g., by mechanically milling or grinding, to a dry particle size of not more than about 50 μm in equivalent spherical diameter do not work as well as polymers made from aqueous suspensions in the ophthalmic vehicle of the invention.

While not being bound by any theory or mechanism advanced to explain the functioning of this invention, one possible explanation for the difference of such mechanically milled or ground polymer particles as the sole particulate polymer present is that grinding disrupts the spatial geometry or configuration of the larger than 50 μm lightly cross-linked polymer particles, perhaps by removing uncross-linked branches from polymer chains; by producing particles having sharp edges or protrusions, or by producing ordinarily too broad a range of particle sizes to afford satisfactory delivery system performance. A broad distribution of particle sizes impairs the viscosity-gelation relationship. In any event, such mechanically reduced particles are less easily hydratable in aqueous suspension than particles prepared to the appropriate size by suspension or emulsion polymerization, and also are less able to gel in the eye under the influence of tear fluid to a sufficient extent and are less comfortable once gelled than gels produced in the eye using the aqueous suspensions of this invention. However, up to about, 40% by weight, e.g., from about 0% to over 20% by weight, based on the total weight of lightly cross-linked particles present, of such milled or ground polymer particles can be admixed with solution or emulsion polymerized polymer particles having dry particle diameters of not more than about 50 μm when practicing this invention. Such mixtures also provide satisfactory viscosity levels in the ophthalmically acceptable vehicle and in the in situ gels formed in the eye coupled with ease and comfort of administration and satisfactory sustained release of the active ingredient to the eye, particularly when such milled or ground polymer particles, in dry form, average from about 0.01 to about 30 μm, and in other embodiments, from about 1 to about 5 μm, in equivalent spherical diameter.

In some embodiments, the particles have a narrow particle size distribution within a 10 μm band of major particle size distribution which contains at least 80%, in other embodiments at least 90%, and in still other embodiments at least 95% of the particles. Also, there is generally no more than about 20%, and in other embodiments no more than about 10%, and in still other embodiments no more than about 5% particles of a size below 1 μm. The presence of large amounts of such fines has been found to inhibit the desired gelation upon eye contact. Apart from that, the use of a monodispersion of particles gives maximum viscosity and an increased eye residence time of the active ingredient in the ophthalmically acceptable vehicle for a given particle size. Monodisperse particles having a particle size of about 30 μm and below are present in some embodiments. Good particle packing is aided by a narrow particle size distribution.

The aqueous suspensions can contain amounts of lightly cross-linked polymer particles ranging from about 0.1% to about 6.5% by weight, and in other embodiments from about 0.5% to about 4.5% by weight, based on the total weight of the aqueous suspension. They can be prepared using pure, sterile water, such as deionized or distilled, having no physiologically or ophthalmologically harmful constituents, and are adjusted to a pH of from about 3.0 to about 6.5, and in other embodiments from about 4.0 to about 6.0, using any physiologically and ophthalmologically acceptable pH adjusting acids, bases or buffers, e.g., acids such as acetic, boric, citric, lactic, phosphoric, hydrochloric, or the like, bases such as sodium hydroxide, sodium phosphate, sodium borate, sodium citrate, sodium acetate, sodium lactate, THAM (trishydroxymethylaminomethane), or the like and salts and buffers such as citrate/dextrose, sodium bicarbonate, ammonium chloride and mixtures of the aforementioned acids and bases.

The second polymer can be any polymer that can enhance the viscosity and mucoadhesive properties of the vehicle where the combination is greater than each individual polymer alone and is also ophthalmically acceptable. Numerous examples of ophthalmically acceptable polymers are disclosed in Wagh et al. Asian J. Pharmaceutics (2008), which is incorporated by reference herein in its entirety. Exemplary second polymers include, without limitation, hydroxyproplymethyl cellulose (HPMC), hydroxypropyl cellulose (HPC), methyl cellulose (MC), hydroxyethyl cellulose (HEC), polyacrylic acid (PAA), polyvinyl alcohol, carbomers, sodium hyaluronate, chitosan, cyclodextrins, polygalacturonic acid, polyitaconic acid, xyloglucan, xanthan gum, gellan gum, polyorthoesters, celluloseacetophthalate, poloxamer 407, polyethyleneimine, and polyethylene oxide. In some embodiments, the second polymer can be a neutral polymer, a cationic polymer, or a second anionic polymer In particular embodiments, the second polymer can be a cationic polymer. Cationic polymers include any ophthalmically acceptable polyamine polymer capable of modulating the Theological and/or mucoadhesive properties of the vehicle. Such polyamines include, for example, poly-L-lysine (PLL), chitosan, a naturally occurring polysaccharide containing D-glucosamine, polyethyleneimine (PEI), and polyquaternium compounds that include but not limited to Polyquaternium 1, Polyquaternium 7, and Polyquarternium 10, Without being bound by theory, a cationic polymer can impact the vehicle characteristics in at least two different ways. Firstly, the cationic polymer can enhance electrostatic interactions between the carrier and the negatively charged mucins of the corneal epithelium. Such an interaction can confer beneficial mucoadhesive properties to the vehicle. Secondly, the viscosity of the aqueous suspension of the carboxy-containing polymer is increased by the addition of a cationic polymer, even prior to administration to the eye. Again, without being bound by theory, the cationic polyamine polymer can assist in particle aggregation through hydrogen bonding and/or by electrostatic interactions to effectively generate larger molecular weight constructs which increase the aqueous suspension's viscosity. In order to realize the benefits of the added cationic polymer, it should present in an amount that allows the particles of the carboxy-containing polymer to remain suspended, since these advantages are lost upon removal of the carboxy-containing particles from a suspended state. The increased viscosity of the dual cationic polymer/carboxy-containing polymer system can also help counter the effects of the clearance mechanisms in the eye.

In some embodiments, the cationic polymer is chitosan. Chitosan is obtained by deacetylation of chitin and possesses mucoadhesive properties due to electrostatic interaction between positively charged chitosan ammonium groups and negatively charged mucosal surfaces. Chitosan is a linear polysaccharide composed of randomly distributed β-(1-4)-linked D-glucosamine and N-acetyl-D-glucosamine. Chitosan is available with varying degrees of deacetylation (% DA) and is generally produced in a range from between about 60 to about 100% deacetylation. The amino group in chitosan has a pKa value of about 6.5, thus, chitosan is positively charged and soluble in acidic to neutral solution with a charge density dependent on pH and the % DA-value. Chitosan can enhance the transport of polar drugs across epithelial surfaces, and is considered biocompatible and biodegradable.

In some embodiments, chitosan used in the vehicle has a molecular weight in a range from between about 50 kDa to about 100 kDa, including any weights in between, while in other embodiments, chitosan used in the vehicle has a molecular weight in a range from between about 1,000 to about 3,000 kDa, and any weights in between. As shown in the Examples below, the range between about 1,000 kDa and about 3,000 kDa appears to have a larger impact on viscosity of the vehicle, even at very small concentrations of the cationic polymer. In order to achieve comparable viscosities with chitosan alone, solutions of chitosan several orders of magnitude more concentrated have been used, for example, from between about 2% to about 4%.

In the ophthalmically acceptable vehicle of the present invention, chitosan or other second polymer is present in an amount ranging from between about 0.01% to about 0.5% when using a cationic polymer having a molecular weight ranging from about 50 kDa to about 100 kDa. The amount of cationic polymer or chitosan can be any amount in between, including about 0.01%, 0.025%, 0.05%. 0.075%, 0.10%, 0.15%, 0.20%, 0.25%, 0.30%, 0.35%, 0.40%, 0.45%, and 0.50% and any amount in between these values. When using higher molecular weight cationic polymers, such as between about 1,000 to about 3,000 kDa, the amount of cationic polymer necessary to achieve favorable viscosities can be substantially reduced. For example, the amount of 1,000 kDa to about 3,000 kDa chitosan can be in a range between about 0.01% and 0.5%, or any amount in between including, for example, 0.01%, 0.015%, 0.020%, 0.025%, 0.030%, 0.035%, 0.040%, 0.045%, 0.05%, 0.1%, 0.15%, 0.20%, 0.25%, 0.30%, 0.35%, 0.40%, 0.45%, and 0.50%.

When formulating the aqueous suspensions of this invention, their osmolality will be adjusted to from about 10 mOsm/kg to about 400 mOsm/kg, and in other embodiments, from about 100 to about 300 mOsm/kg, using appropriate amounts of physiologically and ophthalmologically acceptable salts. Sodium chloride can be used as an osmolality adjusting agent to adjust the osmolality of the aqueous suspension to approximate that of physiologic fluid. The amounts of sodium chloride ranging from about 0.01% to about 1% by weight, and in other embodiments from about 0.05% to about 0.45% by weight, based on the total weight of the aqueous suspension, will give osmolalities within the above-stated ranges. Equivalent amounts of one or more salts made up of cations such as potassium, ammonium and the like and anions such as chloride, citrate, ascorbate, borate, phosphate, bicarbonate, sulfate, thiosulfate, bisulfite and the like, e.g., potassium chloride, sodium thiosulfate, sodium bisulfite, ammonium sulfate, and the like can also be used in addition to or instead of sodium chloride to achieve osmolalities within the above-stated ranges.

The amounts of lightly cross-linked carboxy-containing polymer particles, cationic polymer, the pH, and the osmolality chosen from within the above-stated ranges can be correlated with each other and with the degree of cross-linking to give aqueous suspensions having viscosities ranging from about 1,000 to about 30,000 cps, and in other embodiments from about 5,000 to about 20,000 cps, as measured at room temperature (about 25° C.) using a Brookfield Digital LVT Viscometer equipped with a number 25 spindle and a 13R small sample adapter at 12 rpm. The correlations of those parameters are also such that the suspensions will gel on contact with tear fluid to give gels having viscosities estimated to range from about 75,000 to about 500,000 cps, e.g., from about 200,000 to about 300,000 cps, measured as above, depending on pH as observed, for example, from pH-viscosity curves. This effect is noted by observing a more viscous drop on the eye as a set cast. The cast, after setting, can be easily removed. Alternatively, the viscosity can be from about 1000 to about 5000 cps as measured with a Brookfield cone and plate viscometer DV-II+ with the spindle no. CP-52 at 6 rpm.

In some embodiments, the viscosity is in a range from about 1,000 to about 30,000 cps, and in other embodiment from about 5,000 to about 20,000 cps. In yet other embodiments, the viscosity is in a range from about 10,000 to about 15,000 cps. The viscosity range can also be between about 1,000 and 5,000 cps, including 1,000, 1,500, 2,000, 2,500, 3,000, 3,500, 4,000, 4500, and 5,000 cps and all values in between. The viscosity range can also be between about 5,000 to about 10,000 cps, including 5,000, 5,500, 6,000, 6,500, 7,000, 7,500, 8,000, 8,500, 9,000, 9,500, and 10,000 cps and all values in between. The viscosity range can also be between about 10,000 to about 15,000 cps, including 10,000, 10,500, 11,000, 11,500, 12,000, 12,500, 13,000, 13,500, 14,000, 14,500, and 15,000 cps and all values in between. The viscosity range can also be between about 15,000 to about 20,000 cps, including 15,000, 15,500, 16,000, 16,500, 17,000, 17,500, 18,000, 18,500, 19,000, 19,500, and 20,000 cps and all values in between. The viscosity range can also be between about 20,000 to about 30,000 cps, including 20,000, 21,000, 22,000, 23,000, 24,000, 25,000, 26,000, 27,000, 28,000, 29,000, and 30,000 cps and all values in between. In some embodiments, the ophthalmically acceptable vehicle can include a thickening agent or viscosfier that modulates the viscosity of the vehicle. These include, without limitation, polyethylene glycols, polyvinyl alcohol, polyacrylic acid, polyethylene oxide, and poloxamers.

In some embodiments, the present invention provides a composition that includes the ophthalmically acceptable vehicles described herein along with a medicament for treatment of a disease or disorder, wherein ocular delivery of the medicament is indicated for the treatment of said disease or disorder. Such compositions can also include two or more medicaments that can be used in a combination therapy as discussed further below. Ocular delivery can be indicated for diseases and disorder of the eye and surrounding tissues. One skilled in the art will also recognize the ability to deliver a drug systemically through an ocular route. Such systemic delivery can be useful to treat diseases or disorders beyond the eye itself and its surrounding tissues.

In some embodiments, an effective amount of a medicament is used in conjunction with the ophthalmically acceptable vehicle of the invention. Such formulations can be used for the treatment of an ocular disease and/or prophylaxis against an ocular disease. An effective amount will achieve the goal of preventing, reducing, or eliminating the ocular disease. An effective amount includes from about 1 µg to 10,000 µg per dose in one embodiment, and from about 100 µg to 1000 µg per dose in another embodiment. An effective amount includes all values in between and fractions thereof, for example, about 0.1 µg, 100+1 µg . . . up to about 10000 µg per dose. An effective amount can administered in a dosing regimen once per day, twice per day, thrice per day, or any number of times per day and can be determined in consultation with a physician. An effective amount can be administered as a solution in eye drop form as about a 0.05% to about 5.0% by weight solution of the active ingredient, including for example, about 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.25%, 0.30%, 0.35%, 0.40%, 0.45%, 0.50%, 0.60%, 0.75%, 1.0%, 1.5%, 2.0%, 2.5%, 3.0%, 3.5%, 4.0%, 4.5%, and 5.0%, and all values in between and fractions thereof.

In some embodiments, a medicament, a substance used in treating or ameliorating a disease or medical condition, including drugs intended to treat therapeutically the eye itself or the tissues surrounding the eye and drug administered via the ophthalmic route to treat therapeutically a local condition other than one involving the eye, will typically be incorporated in the ophthalmically acceptable vehicle in therapeutically active amounts comparable to amounts administered in other dosage forms, usually in amounts ranging from about 0.005% to about 10% by weight, and preferably from about 0.01% to about 5% by weight, based on the total weight of the formulation. Thus, for example, from about 0.01% to about 1% by weight of the anti-inflammatory steroid fluorometholone can be administered in this manner.

The vehicle of the present invention can be used in conjunction with therapeutic medicaments for numerous indications. Such medicaments include, without limitation, antibacterial antibiotic agents, antibacterial agents, antifungal antibiotic agents, antifungal agents, antineoplastic agents, steroidal anti-inflammatory agents, non-steroidal anti-inflammatory agents, anti-allergic agents, glaucoma-treating agents, antiviral agents, anti-mycotic agents, anti-infective agents, anti-allergic agents, antiviral agents, anti-glaucoma agents, anesthetic agents, retinal like anti-angiogenesis agents, and agents to treat AMD, diabetic retinopathy, and macular edema.

The vehicle can also include a secondary medicament that can be used in a combination therapy. Such secondary medicaments can be administered in the form of solution-solution, solution suspension, or as suspension-suspension. Exemplary combinations include for example, combinations of two non-steroidal anti-inflammatory agents such as bromfenac and ketorolac, combinations of a nonsteroidal anti-inflammatory agent, such as bromfenac, and a steroid, and bromfenac with other nonsteroidal anti-inflammatory agents and other therapeutic compounds.

An illustrative, but by no means exhaustive listing of such medicaments includes demulcents (for relief of "dry eye"), antibiotics, antivirals, steroids, aminosubstituted steroids, including anti-inflammatory agents, peptides, polypeptides, cardiotonics, antihypertensives, antiallergics, alpha- and betaadrenergic blocking agents, ophthalmic medicaments such as anticataract agents, antiglaucoma agents and ophthalmic antiinflammatory agents, ophthalmic lubricating agents, ophthalmic topical or regional anesthetic agents, etc. Specific medicaments that can be used in the present invention include drugs such as pilocarpine, idoxuridine, carbachol, bethanechol, timolol, atenolol, labetolol, metoprolol, nadolol, oxprenolol, pindolol, sotalol, betaxolol, acebutolol, alprenolol, levo-bunolol, p-aminoclonidine, dipivefrin, tetracycline, epinephrine, phenylephrine, eserine, phospholine, aceclidine, demecarium, cyclopentolate, homatropine, scopolamine, nitroglycerin, ethacrynic acid, furosemide, amiloride, chlortetracycline, bacitracin, neomycin, polymyxin, polymyxin B, gramicidin, oxytetracycline, chloramphenicol, gentamycin, penicillins, erythromycin, sulfacetamide, tobramycin, trospectomycin, vancomycin, ciprofloxacin, perfloxacin, olfloxacin, enoxacin, naphazoline hydrochloride, clindamycin, isofluorophate, fluorometholone, dexamethasone, hydrocortisone, fluorocinolone, medrysone, prednisolone, prednisolone acetate, methylprednisolone, fluticasone propionate, betamethasone, triamcinolone, estradiol, ibuprofen, flurbiprofen, naproxen, esters of ibuprofen, flurbiprofen, and naproxen; ketorolac, suprofen, interferons, cromolyn, gancyclovir, aminozolamide, alltrans-retinoic acid (Vitamin A) and the nontoxic, pharmaceutically acceptable salts thereof. Pro-drug counterparts are also within the scope of the present invention. Ophthalmic lubricating agents are materials capable of inducing natural lacrimation or creating artificial lacrimation and include, for example, polyvinylalcohol, cellulose polymers such as hydroxypropyl methyl cellulose, polylactams such as polyvinylpyrrolidone and the like. "Dry eye" formulations that comprise pure water and a lightly crosslinked polymer of the type described hereinabove in an amount within the range also set forth hereinabove, hypotonic in saline and thus having the requisite osmotic pressure but at a pH in the range of about 3 to about 6.5, are also contemplated as being within the scope of this invention. Topical or regional anesthetic agents include ones used during ophthalmic surgery or other ophthalmic procedures, such as lidocaine, cocaine, benoxinate, dibucaine, proparacaine, tetracaine, etidocaine, procaine, hexylcaine, bupivacaine, mepivacaine, prilocaine, chloprocaine, and the like.

In some embodiments, the medicament is a glucocorticoid including, for example, hydrocortisone, cortisone acetate, prednisone, prednisolone, methylprednisolone, dexamethasone, betamethasone, triamcinolone, and beclomethasone, fluorometholone. Other glucocorticoids include, for example, 21-acetoxypregnenolone, alclometasone, algestone, amcinonide, budesonide, chloroprednisone, clobetasol, clobetasone, clocortolone, cloprednol, corticosterone, cortisone, cortivazol, deflazacort, desonide, desoximetasone, diflorasone, diflucortolone, difluprednate, enoxolone, fluazacort, flucloronide, flumethasone, flunisolide, fluocinolone acetonide, fluocinonide, fluocortin butyl, fluocortolone, fluperolone acetate, fluprednidene acetate, fluprednisolone, flurandrenolide, fluticasone propionate, formocortal, halcinonide, halobetasol propionate, halometasone, halopredone acetate, hydrocortarnate, loteprednol etabonate, mazipredone, medrysone, meprednisone, mometasone furoate, paramethasone, prednicarbate, prednisolone 25-diethylamino-acetate, prednisolone sodium phosphate, prednival, prednylidene, rimexolone, tixocortol, triamcinolone acetonide, triamcinolone benetonide, triamcinolone hexacetonide, their opthalmically acceptable salts, combinations thereof, and mixtures thereof. In one embodiment, the glucocorticoid includes dexamethasone, prednisone, prednisolone, methylprednisolone, medrysone, triamcinolone, loteprednol etabonate, opthalmically acceptable salts thereof, combinations thereof, and mixtures thereof.

Other useful compounds that can be used in conjunction with the ophthalmically acceptable vehicle of the invention include non-steroidal anti-inflammatory drugs (NSAIDs) such as bromfenac, diclofenac, and ketorolac. Suitable NSAIDs for combination therapy are, for example, aspirin, benoxaprofen, benzofenac, bucloxic acid, butibufen, carprofen, ciclofenac, cinmetacin, clidanac, clopirac, diclofenac, diflupredinate, etodolac, fenbufen, fenclofenac, fenclorac, fenoprofen, fentiazac, flunoxaprofen, furaprofen, flurbiprofen, furobufen, furofenac, ibuprofen, ibufenac, indomethacin, indoprofen, isoxepac, ketorolac, ketoprofen, lactorolac, lonazolac, metiazinic, miroprofen, nepafenac, naproxen, norketotifen, oxaprozin, oxepinac, phenacetin, pirprofen, pirazolac, protizinic acid, sulindac, suprofen, tiaprofenic acid, tolmetin, and zomepirac.

Examples of the steroidal anti-inflammatory agents include, but are not limited to: 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, difluprednate, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

Examples of the antifungal antibiotics include, but are not limited to: polyenes (e.g., amphotericin b, candicidin, dennostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin). Examples of the synthetic antifungals include, but are not limited to: allylamines (e.g., butenafine, naftifine, terbinafine), imidazoles (e.g., bifonazole, butoconazole, chlordantoin, chlormiidazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate).

Examples of the antibacterial antibiotics include, but are not limited to: aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), .beta.-lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefmetazole, cefininox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, meziocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin).

Examples of the synthetic antibacterials include, but are not limited to: 2,4-diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., besifloxacin, cinoxacin, ciprofloxacin, clinafloxacin, difloxacin, enoxacin, fleroxacin, flumequine, gatifloxacin, garenoxacin, grepafloxacin, lomefloxacin, miloxacin, moxifloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine-t, n.sup.2-formylsulfisomidine, n.sup.4-.beta.-d-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, 4-sulfanilamidosalicylic acid, n.sup.4-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine, xibomol).

In some embodiments the active ingredient is present in a range from about 0.05% to about 5.0% by weight, while in other embodiments the active ingredient is present in a range from about 0.08% to about 0.12% by weight. The amount of active ingredient based on weight percent can be any value between these values, including for example, 0.05%, 0.060%, 0.07%, 0.08%, 0.09%, 0.10%, 0.11%, 0.12%, 0.13%, 0.14%, 0.15%, 0.16%, 0.17%, 0.18%, 0.19%, 0.20%, 0.25%, 0.30%, 0.35%, 0.40%, 0.45%, 0.50%, 0.60%, 0.75%, 1.0%, 1.5%, 2.0%, 2.5%, 3.0%, 3.5%, 4.0%, 4.5%, and 5.0% by weight and all values in between and fractions thereof.

The viscous gels that result upon administration of the aqueous suspensions of this invention to the eye have residence times in the eye ranging from about 2 to about 12 hours, e.g., from about 3 to about 6 hours. The active ingredients contained in these ophthalmically acceptable vehicles are released from the gels at rates that depend on such factors as the active ingredient itself and its physical form, the extent of drug loading and the pH of the system, as well as on any drug delivery adjuvants, such as ion exchange resins compatible with the ocular surface, which can also be present. For fluorometholone, for example, release rates in the rabbit eye in excess of four hours, as measured by fluorometholone contained in the aqueous humor, have been observed.

The active ingredient-ophthalmically acceptable vehicle can be formulated in any of several ways. For example the active ingredient, lightly cross-linked polymer particles, and osmolality-adjusting agent can be pre-blended in dry form, added to all or part of the water, and stirred vigorously until apparent polymer dispersion is complete, as evidenced by the absence of visible polymer aggregates. Sufficient pH adjusting agent is then added incrementally to reach the desired pH, and more water to reach 100 percent formula weight can be added at this time, if necessary. Another convenient method involves adding the drug to about 95 percent of the final water volume and stirring for a sufficient time to saturate the solution. Solution saturation can be determined in any known manner, e.g., using a spectrophotometer. The lightly cross-linked polymer particles and the osmoiality-adjusting agent are first blended in dry form and then added to the drug-saturated suspension and stirred until apparent polymer hydration is complete. Following the incremental addition of sufficient pH adjusting agent to reach the desired pH, the remainder of the water is added, with stirring, to bring the suspension to 100 percent formula weight.

These aqueous suspensions can be packaged in preservative-free, single-dose non-reclosable containers. This permits a single dose of the active ingredient to be delivered to the eye one drop at a time, with the container then being discarded after use. Such containers eliminate the potential for preservative-related irritation and sensitization of the corneal epithelium, as has been observed to occur particularly from ophthalmic medicaments containing mercurial preservatives. Multiple-dose containers can also be used, if desired, particularly since the relatively low viscosities of the aqueous suspensions of this invention permit constant, accurate dosages to be administered dropwise to the eye as many times each day as necessary.

In those vehicles where preservatives are to be included, suitable preservatives are chlorobutanol, Polyquat, benzalkonium chloride, cetyl bromide, benzethonium chloride, cetyl pyridinium chloride, benzyl bromide, EDTA, phenylmercury nitrate, phenylmercury acetate, thimerosal, merthiolate, acetate and phenylmercury borate, chlorhexidine, polymyxin B sulphate, methyl and propyl parabens, phenylethyl alcohol, quaternary ammonium chloride, sodium benzoate, sodium proprionate, sorbic acid, and sodium perborate. In particular embodiments, the preservative includes benzalkonium chloride.

In some embodiments, the preservative is present in a range from about 0.001 to about 0.02% by weight. The preservative can be present at about 0.001, 0.002, 0.003, 0.004, 0.005% and any amount in between these amounts. In particular, the present invention has the benefit of substantial reduction in the use of a bactericidal component. Thus, in some embodiments, the present invention provides an ophthalmically acceptable vehicle having less than about 0.01% of a preservative with bactericidal activity in one embodiment, and less than about 0.01%, 0.009%, 0.008%, 0.007%, 0.006%, 0.005%, 0.004%, 0.003%, or 0.002%, in other embodiments.

In some embodiments, the ophthalmically acceptable vehicle includes a wetting agent. Such agents can be useful in distributing the active ingredient in an otherwise predominantly aqueous environment. Such wetting agents include, for example, Poloxamer 407, a triblock copolymer consisting of a central hydrophobic block of polypropylene glycol flanked by two hydrophilic blocks of polyethylene glycol. Other wetting agents that can be used include carboxymethylcellulose, hydroxypropyl methylcellulose, glycerin, mannitol, polyvinyl alcohol, Octoxynol 40 and hydroxyethylcellulose.

The composition containing a medicament and an ophthalmically acceptable vehicle can be individually packaged for a single dose administration; e.g., in a bottle, jar, ampoule, tube, syringe, envelope, container, unit dose container or vial. When the composition is individually packaged, in some embodiments, the composition does not include a preservative. Alternatively, the composition can be contained in a package that is capable of holding multiple units; e.g., in resealable glass or plastic eyedropper bottles.

It is understood that modifications which do not substantially affect the activity of the various embodiments of this invention are also included within the definition of the invention provided herein. Accordingly, the following examples are intended to illustrate but not limit the present invention.

EXAMPLE I

Polymer Screening

This Example shows the varying effects of neutral, anionic and cationic additives to the viscosity of a commercially available carboxy-containing polymer ophthalmic vehicle, DURASITE®.

The screening study was conducted to identify a polymer that could significantly increase the viscosity of a carboxy-containing polymer ophthalmic vehicle. The test polymers included an anionic polymer (polyacrylic acid, 450 kDa), neutral polymer (polyvinyl alcohol, 5 kDa and 133 kDa, or polyethylene oxide 900 kDa) and a cationic polymer (chitosan 50-100 kDa and 1000-3000 kDa).

The test polymer was dissolved in a solution containing citric acid, sodium citrate, mannitol, BAC, and poloxamer 407. Polycarbophil was separately dispersed in a solution containing sodium chloride and edetate disodium dihydrate. The solutions were combined and adjusted to pH 5.0 and q.s.'ed to weight. Small aliquots of the formulation were obtained and the pHs were adjusted to their target values using sodium hydroxide. The viscosities of the resulting vehicles were tested on a rheometer at a shear rate of 12 cycles/second.

The effects of a second polymer on the viscosity of DURASITE® are presented in Table 1 as a function of pH. Included in Table 2 are the viscosities of polycarbophil at pH 7 with and without additive polymer. The anionic polymer polyacrylic acid (PAA) was shown to have a viscosity thinning effect on DURASITE®. The neutral polymers polyvinyl alcohol and polyethylene oxide were shown to exhibit some viscosity thickening effect which was concentration dependent. The cationic polymer chitosan was shown to have the most significant viscosity thickening effect.

TABLE 1

Viscosity as a Function of pH with Additive Polymer

| | | | | | Viscosity (cps) | | | |
|---|---|---|---|---|---|---|---|---|
| pH | DURASITE ® | DURASITE ® + 0.1% PVA (25 kDa) | DURASITE ® + 0.2% PVA (25 kDa) | DURASITE ® + 0.2% PVA (133 kDa) | DURASITE ® + 0.4% PAA (450 kDa) | DURASITE ® + 0.4% PEO (900 kDa) | DURASITE ® + 0.2% CTS (50-100 kDa) |
| 5.0 | 557 | 500 | 554 | 629 | 387 | 909 | 946 |
| 6.0 | 1029 | 967 | 1040 | 1162 | 620 | 1212 | 1259 |
| 6.5 | 1098 | 860 | 1131 | 1164 | 678 | 1254 | 1368 |
| 7.0 | 1097 | 1066 | 1146 | 1191 | 727 | 1271 | 1581 (pH 7.3) |
| 8.0 | 1188 | 1063 | 1153 | 1243 | 696 | 1287 | NT |
| Ref. | 949-47-1 | 949-50-1 | 949-57-1 | 949-65-1 | 949-72-1 | 949-79-1 | 949-91-1 |

NT: not tested

TABLE 2

Effect of Secondary Excipient on Viscosity of DuraSite at pH 7

| | Viscosity (cps) | |
|---|---|---|
| Secondary Excipient | Without DuraSite | With DuraSite |
| Water | <10 | 1097 |
| 0.1% PVA (LMW) | <10 | 1066 |

TABLE 2-continued

Effect of Secondary Excipient on Viscosity of DuraSite at pH 7

| Secondary Excipient | Viscosity (cps) Without DuraSite | Viscosity (cps) With DuraSite |
|---|---|---|
| 0.2% PVA (LMW) | <10 | 1146 |
| 0.2% PVA (HMW) | <10 | 1191 |
| 0.4% PAA | <10 | 727 |
| 0.4% PEO | <10 | 1271 |
| 0.1% CTS (LMW) | <10 | 1225 |
| 0.2% CTS (LMW) | <10 | 1581 |

Small aliquots of the formulation were obtained and their pHs were adjusted to target values using sodium hydroxide. The viscosities of the resulting vehicles were tested on a rheometer at a shear rate of 12 cycles/second.

The effects of concentration and molecular weight on the viscosity of DURASITE® are presented in Table 3. Increasing the concentration of chitosan effectively increased the viscosity of DURASITE®. Similarly, increasing the molecular weight of chitosan increased the viscosity of DURASITE®. The high molecular weight chitosan (1000-3000 kDa) at 0.025% w/w was shown to have the same effect on the viscosity of DURASITE® as the low molecular weight chitosan (50-100 kDa) at 0.4% w/w. The viscosity of DURASITE® was found to increase by approximately two fold at the aforementioned chitosan concentrations.

TABLE 3

Effect of Chitosan (CTS) Concentration, Molecular Weight and pH on the Viscosity of DuraSite ®

| pH | DURASITE ® | DURASITE ® + 0.1% CTS (50-100 kDa) | DURASITE ® + 0.2% CTS (50-100 kDa) | DURASITE ® + 0.4% CTS (50-100 kDa) | DURASITE ® + 0.025% CTS (1000-3000 kDa) | |
|---|---|---|---|---|---|---|
| 5.0 | 557 | 693 | 946 | 1211 | 1332 | 1441 |
| 5.5 | NT | 1014 | 1237 | 1760 | 1877 | 1789 |
| 6.0 | 1029 | 1145 | 1259 | 1781 | 1961 | 2223 |
| 6.5 | 1098 | NT | 1368 | 2073 | 2026 | 2342 |
| 7.0 | 1097 | 1225 | NT | 2252 | 2112 | 2470 |
| 7.5 | NT | 1282 | 1581 (pH 7.3) | NT | NT | 2609 |
| 8.0 | 1188 | 1300 | 1153 | 2747 | 2750 | 2880 |
| References | 949-47-4 | 949-96-1 | 949-91-1 | 953-10-01 | 953-59-01 | 953-62-01 |

NT: not tested

TABLE 2-continued

Effect of Secondary Excipient on Viscosity of DuraSite at pH 7

| Secondary Excipient | Viscosity (cps) Without DuraSite | Viscosity (cps) With DuraSite |
|---|---|---|
| 0.4% CTS (LMW) | <10 | 1803 |
| 0.025% CTS (HMW) | <10 | 2470 |

PVA (LMW): low molecular weight polyvinyl alcohol (25 kDa)
PVA (LMW): high molecular weight polyvinyl alcohol (133 kDa)
PAA: polyacrylic acid (450 kDa)
PEO: polyethylene oxide (900 kDa)
CTS (LMW): low molecular weight chitosan (50-100 kDa)
CTS (HMW): high molecular weight chitosan (1,000-3,000 kDa)

Chitosan had a significant effect on the viscosity of the DURASITE® vehicle. Being a mucoadhesive agent, when formulated with DURASITE®, chitosan has the potential to prolong the retention time of DURASITE® in the eye.

EXAMPLE II

Chitosan Assessment

This Example shows the effect of chitosan concentration and molecular weight on the viscosity of DURASITE®.

Chitosan was dissolved in a solution containing citric acid, sodium citrate dihydrate, mannitol, and poloxamer 407. Polycarbophil was separately dispersed in a solution containing edetate disodium dihydrate and sodium chloride. The chitosan and polycarbophil solutions were brought to the same pH using either hydrochloric acid or sodium hydroxide. The solutions were then combined and water is added to weight.

While both concentration and molecular weight of chitosan had significant effects on the viscosity of DURASITE®, molecular weight appeared to have a much greater effect on the viscosity than concentration. The high molecular weight chitosan (1000-3000 kDa) was highly effective in increasing the viscosity of DURASITE®.

EXAMPLE III

Physical Stability of Chitosan/DURASITE® Formulation

This Example shows the physical stability of a DURASITE® vehicle containing 0.025% high molecular weight chitosan.

The DURASITE® vehicles formulated to target pHs of 5.0, 6.5, and 8.0 were filled into Type I glass vials and crimped with Teflon-coated rubber caps. The test samples were placed in stability chambers set at 5° C. and 25° C. The physicochemical attributes of the vehicle (i.e. viscosity, pH, osmolality) were tested on a monthly basis.

The physicochemical stability of the 0.025% chitosan in DURASITE® tested up to 2 months is shown in Table 3. Except for the viscosity of the pH 6.5 sample stored at 25° C., all physicochemical attributes of the other samples remained the same through 2 months at 5° C. and 25° C. The pH 6.5 stability sample stored at 25° C. for 1 month was shown to have a higher viscosity value than those at the other storage condition and time points and appeared to be an outlier.

TABLE 4

| Test Parameter | Test Interval | pH 5.0 | pH 6.5 | pH 8.0 |
|---|---|---|---|---|
| Viscosity (cps) | Initial | 1049 | 1794 | 2964 |
| | 1 month, 5° C. | 962 | 1896 | 3129 |
| | 1 month, 25° C. | 1137 | 2575 | 3128 |
| | 2 months, 5° C. | 1224 | 2169 | 2944 |
| | 2 months, 25° C. | 1048 | 1950 | 2892 |
| pH | Initial | 5.0 | 6.5 | 8.0 |
| | 1 month, 5° C. | 4.9 | 6.5 | 8.0 |
| | 1 month, 25° C. | 5.0 | 6.4 | 7.9 |
| | 2 months, 5° C. | 5.0 | 6.5 | 8.0 |
| | 2 months, 25° C. | 5.0 | 6.5 | 8.0 |
| Osmolality (mOsm/kg) | Initial | 279 | 285 | 284 |
| | 1 month, 5° C. | 279 | 285 | 285 |
| | 1 month, 25° C. | 279 | 285 | 284 |
| | 2 months, 5° C. | 280 | 286 | 286 |
| | 2 months, 25° C. | 279 | 285 | 286 |

EXAMPLE IV

Effect of Chitosan on the Drug Release Rate of Azithromycin from DURASITE®

This Example shows the effect of chitosan on the release rate of azithromycin from DURASITE®.

The in vitro release rates of azithromycin from two DURASITE® formulations containing 1% azithromycin were studied. One formulation was formulated with 0.025% high molecular weight (1,000-3,000 kDa) chitosan, and one without chitosan. Approximately 100 mg of the formulation was placed in a flow-through cell containing phosphate buffer saline operating at a flow rate of approximately 6 mL/hour. The flow-cell was attached to a UV/Vis spectrophotometer that measured the concentration of azithromycin in the phosphate buffer saline solution as a function of time. The effect of chitosan on the release rate of azithromycin from DuraSite is shown in FIG. 1. Both formulations were shown to exhibit good release rate over the 5-hour duration studied. In addition, the DuraSite formulation containing chitosan was shown to have a higher initial release rate and higher sustained release rate throughout the study.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. An ophthalmically acceptable drug delivery vehicle, comprising:
   an aqueous suspension having a first viscosity, said suspension comprising from about 0.1% to about 6.5% by weight, based on the total weight of the suspension, of a polycarbophil prepared by polymerizing one or more carboxyl-containing monoethylenically unsaturated monomers and less than about 5% by weight of a cross-linking agent, said weight percentages of monomers being based on the total weight of monomers polymerized, said polycarbophil having average particle size of not more than about 50 μm in equivalent spherical diameter, and no more than 5% of said polycarbophil has a particle size below 1 μm, and;
   a sufficient amount of chitosan to allow said polycarbophil to remain suspended,
   wherein upon contact with tear fluid, said vehicle gels to a second viscosity which is greater than the first viscosity.

2. The vehicle of claim 1, wherein the chitosan has a molecular weight in the range of from about 1000 to 3000 kDa and is present in a range from between about 0.01% to about 0.15% by weight.

3. The vehicle of claim 1, wherein the chitosan has a molecular weight of from about 50 to 100 kDa and is present in a range from between about 0.01% and about 0.4% by weight.

4. A composition comprising the ophthalmically acceptable vehicle of claim 1 and a medicament for treatment of a disease or disorder, wherein ocular delivery of said medicament is indicated for the treatment of said disease or disorder.

5. The composition of claim 4, wherein the composition further comprises an ophthalmically acceptable salt in an amount of from about 0.01% to about 1% by weight, based on the total weight of the composition.

6. The composition of claim 4, wherein said medicament is present in an amount of from about 0.005% to about 10% by weight, based on the total weight of the composition.

7. The composition of claim 4, wherein said medicament is selected from the group consisting of an antibacterial antibiotic agent, an antibacterial agent, an antifungal antibiotic agent, an antifungal agent, an antineoplastic agent, a steroidal anti-inflammatory agents, a nonsteroidal anti-inflammatory agent, an anti-allergic agent, a glaucoma-treating agent, an antiviral agent, an anti-mycotic agent, an anti-infective agent, an anti-allergic agent, an antiviral agent, an anti-glaucoma agent, an anesthetic agent, a retinal like anti-angiogenesis agent, an agent to treat AMD, an agent to treat diabetic retinopathy, an agent to treat macular edema, and combinations thereof.

8. The composition of claim 7, wherein the composition comprises at least two medicaments.

9. The composition of claim 8, wherein said at least two medicaments are different nonsteroidal anti-inflammatory agents.

10. The composition of claim 8, wherein said at least two medicaments are a non-steroidal anti-inflammatory agent and a steroidal anti-inflammatory agent.

11. The composition of claim 4 further comprising a preservative.

12. The composition of claim 4 further comprising a thickener.

13. The composition of claim 4 further comprising a wetting agent.

14. A method of administering a medicament to the eye of a subject comprising applying to the eye of a subject a composition comprising the ophthalmically acceptable vehicle of claim 1 and a medicament contained therein for treatment of a disease or disorder for which ophthalmic delivery is indicated;
   wherein said medicament is released from the vehicle in a sustained release manner.

15. The vehicle of claim 4 wherein the medicament is ketorolac.

16. The vehicle of claim 15 wherein the ketorolac is present in the composition in an amount of about 0.4% by weight based on the total weight of the composition.

17. The vehicle of claim 15 wherein the ketorolac is present in the composition in an amount of about 0.2% by weight based on the total weight of the composition.

* * * * *